(12) United States Patent
Ju et al.

(10) Patent No.: US 11,559,342 B2
(45) Date of Patent: Jan. 24, 2023

(54) DELIVERY TOOL AND METHOD FOR FORMING A STRUCTURE HAVING A LAYER OF HARDENED PASTE AND PARTICLES UNDER THE LAYER

(71) Applicant: JOY MEDICAL DEVICES CORPORATION, Kaohsiung (TW)

(72) Inventors: Chien-Ping Ju, Kansas City, MO (US); Jiin-Huey Chern Lin, Winnetka, IL (US); Bing-Chen Yang, Kaohsiung (TW); Yen-Chun Chen, Kaohsiung (TW)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 211 days.

(21) Appl. No.: 16/877,528

(22) Filed: May 19, 2020

(65) Prior Publication Data

US 2020/0367953 A1 Nov. 26, 2020

Related U.S. Application Data

(60) Provisional application No. 62/852,373, filed on May 24, 2019.

(51) Int. Cl.
*A61B 17/88* (2006.01)

(52) U.S. Cl.
CPC ...... *A61B 17/8816* (2013.01); *A61B 17/8822* (2013.01)

(58) Field of Classification Search
CPC ............ A61F 2/4601; A61F 2002/4625; A61F 2002/4627; A61F 2002/4635; A61N 17/8805; A61N 17/8802; A61N 17/8833; A61N 17/8811; A61N 17/8816; A61N 17/8819; A61N 17/8822; A61N 17/8825
See application file for complete search history.

(56) References Cited

U.S. PATENT DOCUMENTS

2014/0277486 A1* 9/2014 Abdou ................ A61F 2/4465
623/17.16
2016/0106551 A1* 4/2016 Grimberg, Jr ........ A61F 2/4601
623/17.16

* cited by examiner

*Primary Examiner* — Amy R Sipp
(74) *Attorney, Agent, or Firm* — Bacon & Thomas, PLLC

(57) ABSTRACT

The present invention provides a delivery tool and a method for bone grafting on a bone surface via a minimally invasive approach, wherein a structure having a layer of hardened paste and particles under the layer is formed by using the delivery tool. The layer helps to keep particles on the bone surface.

12 Claims, 8 Drawing Sheets

DELIVERY TOOL AND METHOD FOR FORMING A STRUCTURE HAVING A LAYER OF HARDENED PASTE AND PARTICLES UNDER THE LAYER

FIELD OF THE INVENTION

The present invention is related to a technique for forming a structure having a layer of hardened paste and particles under the layer on a bone surface via a minimally invasive approach, and in particular this technique is very useful in dental ridge augmentation, and also in bone augmentation/thickening for orthopedic applications.

BACKGROUND OF THE INVENTION

The conventional procedure of dentoalveolar bone grafting is conducted by first creating a rectangular-shaped flap through one crest incision accompanied with two vertical releasing incisions to expose the bony defect, followed by the placement of bone graft (powder or block) into the bone defect. To avoid migration of the graft, a barrier membrane or bone screws are often used to fix the implant before the primary closure with tension-free, water-tight suture. Not only costly and time-consuming, the crest incision made right on top of the bony defect in this conventional procedure largely increases dehiscence and infection risks. Another often-encountered problem with the conventional flap surgery is in its difficult suture procedure involving cutting through periosteum and dissecting soft tissues to extend flap that would otherwise be difficult to close the wound due to the readily infilled bone graft. This, in turn, can cause more post-operative swelling/pain to the patient.

In addition to dental ridge augmentation, there is also a need for bone augmentation/thickening in plastic surgery. It would be more advantageous, if these augmentations can be carried out via a minimal incision. However, there is no delivery tool to fulfill this need.

SUMMARY OF INVENTION

A primary objective of the present invention is to provide a delivery tool free of the above-mentioned drawbacks, which is able to be used for dental ridge augmentation and bone augmentation/thickening in orthopedic applications, such as plastic surgery, via a minimal incision.

Another objective of the present invention is to provide a method for bone grafting on a bone surface via a minimally invasive approach by forming a structure comprising a layer of hardened paste and particles under the layer.

Preferred embodiments of the present invention include (but not limited to) the features recited in the accompanied claims.

BRIEF DESCRIPTION OF THE DRAWINGS

In FIG. 1 to FIG. 8 the like elements or parts are represented by like numerals.

DETAILED DESCRIPTION OF THE INVENTION

Figure 1:
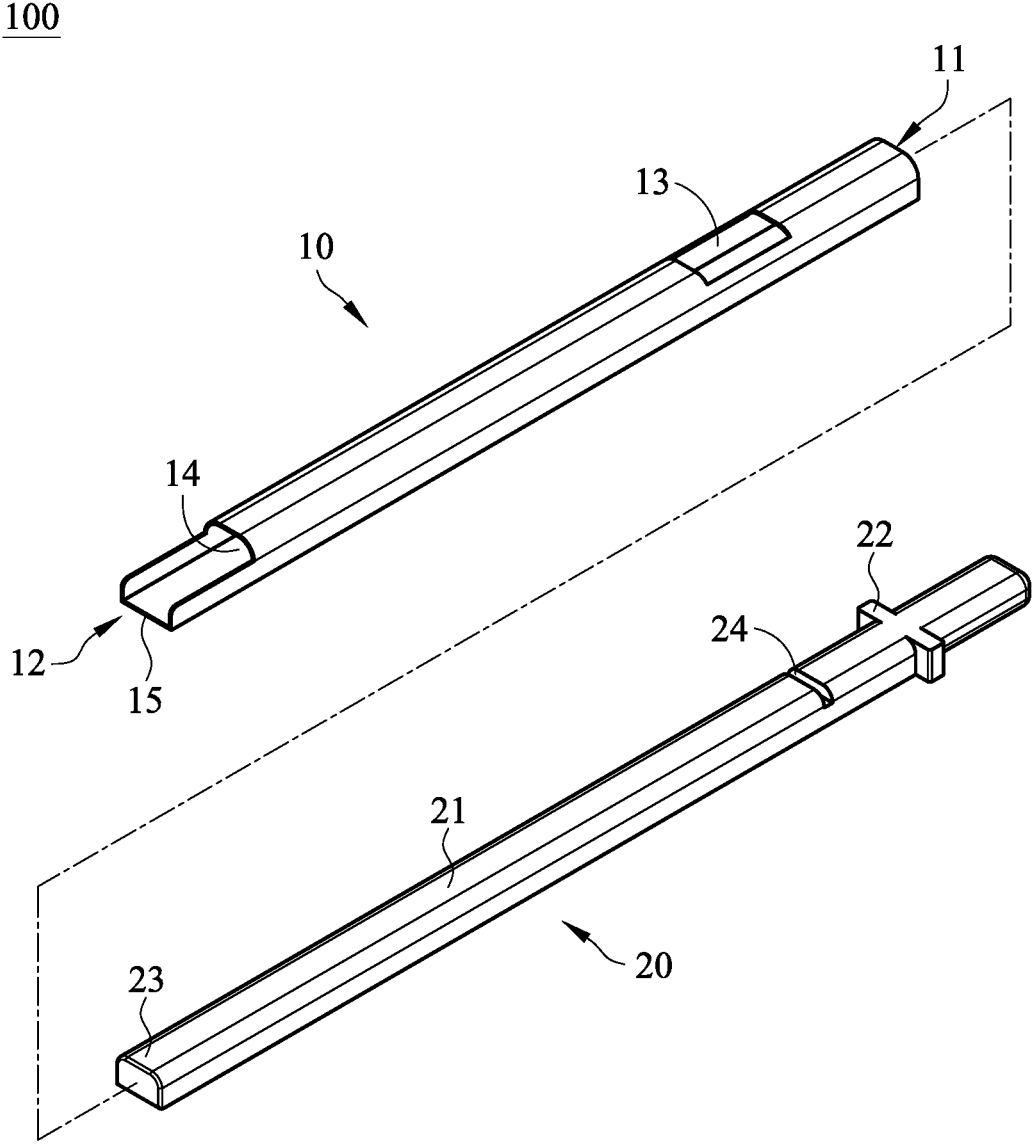
FIG. 1 shows a perspective view of a delivery tool constructed according to a first preferred embodiment of the present invention.

A delivery tool 100 suitable for forming a structure comprising a layer of hardened paste and particles under the layer constructed according to a first preferred embodiment of the present invention is shown in FIG. 1, which has a straight hollow tube 10 and a corresponding plunger 20 for pushing material filled in a channel of the hollow tube. The channel may have a rectangular cross-section. The hollow tube has a plunger inlet 11 at the right end, a filler outlet 12 at the left end, and a filler inlet 13, wherein the filler inlet 13 is the plunger inlet 11 or is formed at a location closer to the plunger inlet 11 than to the filler outlet 12 of the hollow tube, wherein the filler outlet 12 has an opening 14 and a U-shaped drain 15 extending from the opening. The filler inlet 13 and the U-shaped drain 15 have different opening directions, which may be opposite to one another, or may form an angle such as between 20 and 160 degrees.

The plunger 20 has an insertion portion 21 which has a cross-section slightly smaller than a cross-section of the channel of the hollow tube 10, and a stop protrusion 22 which has a cross-section larger than the cross-section of the channel of the hollow tube, so that the insertion portion 21 of the plunger is able to be inserted into the channel of the hollow tube 10 via the plunger inlet 11. The insertion portion 21 of the plunger has a head 23 at its front end (left end), and the head 23 thereof will pass the filler inlet 13, and then occupy the U-shaped drain 15 of the filler outlet 12, when the insertion portion 21 of the plunger 20 is inserted into the channel of the hollow tube 10 until the stop protrusion 22 contacts the plunger inlet 11 of the hollow tube 10. The plunger 20 may have a uniform cross-section between the head 23 and the stop protrusion 22.

A suitable amount of a bone cement paste is introduced into the channel of the hollow tube 10 via the filler inlet 13, and then the insertion portion 21 of the plunger 20 is inserted into the channel of the hollow tube 10 via the plunger inlet 11 until the stop protrusion 22 contacts the plunger inlet 11 of the hollow tube 10. When the cement paste exits the opening 14 of the filler outlet 12, it can flow forward and upward while the head 23 of the plunger 20 invading the U-shaped drain 15 of the hollow tube 10. If the left end of the hollow tube 10 is covered by a tissue, e.g. a periosteum, of a patient with an opening space of the U-shaped drain 15 of the hollow tube 10 facing the tissue, a substantial portion of the cement paste will be forced to flow on top of the head 23 of the plunger 20 toward the tissue, and it will often surgically lift, the tissue as the stop protrusion 22 contacts the plunger inlet 11 of the hollow tube 10. Said substantial portion of the cement paste will then be confined and hardened in a space between the head 23 of the plunger 20 and said tissue, forming a hardened "roof". It is desired that the confined bone cement paste becomes hardened or substantially hardened within a short period of time, such as 1-20 minutes, preferably less than 10 minutes, and more preferably less than 5 minutes, and thus a layer of a hardened bone cement paste is formed in the confined space. The plunger 20 will then be withdrawn to expose the filler inlet 13 of the hollow tube 10, leaving the layer of the hardened bone cement paste under the tissue.

Bone graft particles, preferably porous particles, are introduced into the channel of the hollow tube 10 via the filler inlet 13 in an amount equivalent to or slightly less than a volume of the opening space of the U-shaped drain 15. The plunger further has a mark 24 on the top side of the insertion portion 21, so that the particles can advance in the channel of the hollow tube 10 and fully fill the opening space of the U-shaped drain 15 under the layer of the hardened bone cement paste (the "roof"), when the insertion portion 21 of the plunger 20 is inserted into the channel of the hollow tube 10 and the mark 24 reaches the plunger inlet 11 of the hollow tube 10.

The hollow tube 10 together with the plunger 20 under the tissue are now can be removed, and a structure having a layer of hardened bone cement paste and bone graft particles under the layer is formed under the tissue. The bone graft particles would be on a surface of a bone without periosteum, if the tissue is periosteum lifted from the bone.

Figure 2:
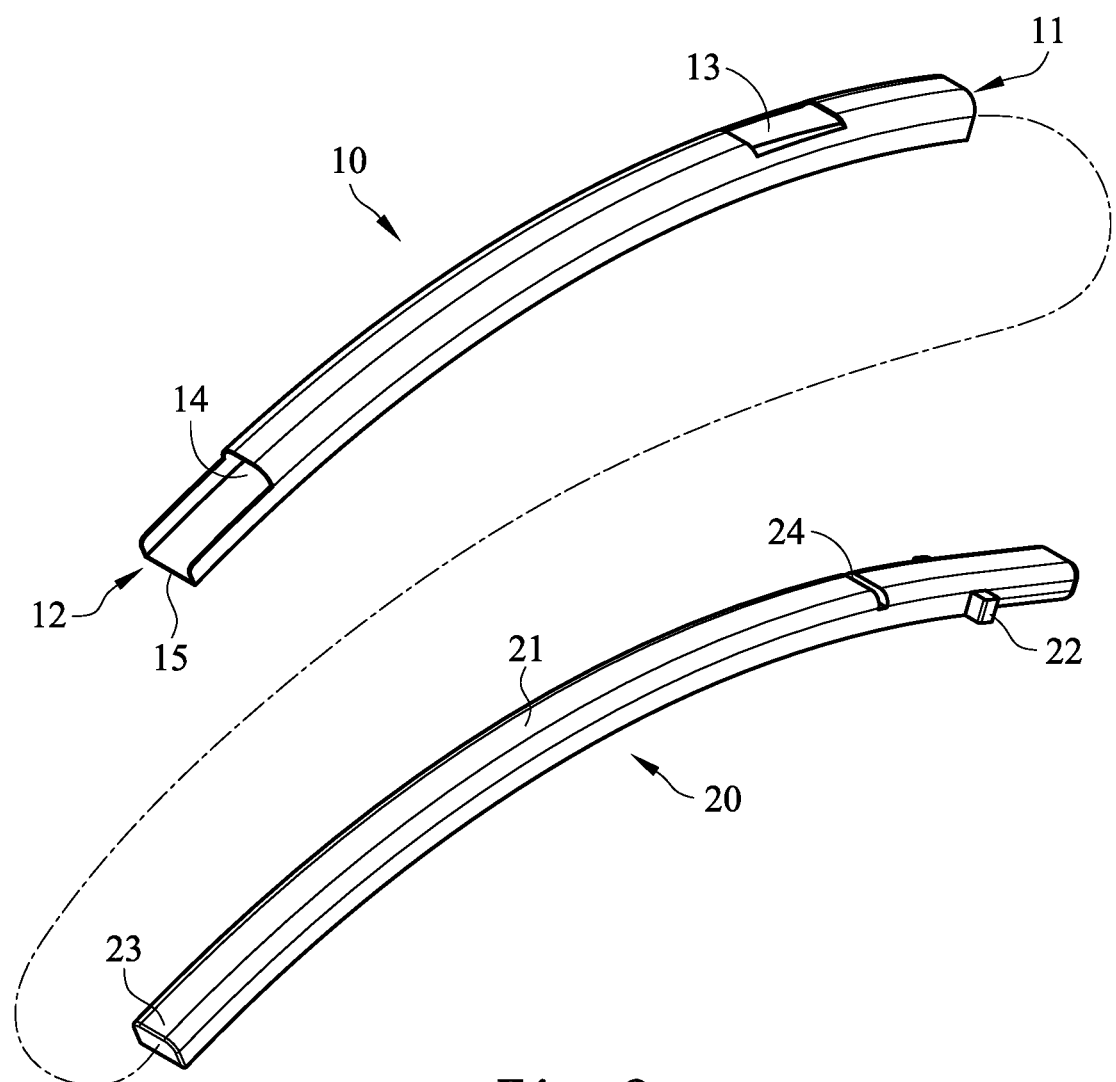
FIG. 2 shows a perspective view of a delivery tool constructed according to a second preferred embodiment of the present invention.

FIG. 2 shows a delivery tool 100 constructed according to a second preferred embodiment of the present invention, which is similar to the first preferred embodiment shown in FIG. 1 except the shape. The delivery tool 100 constructed according to the second preferred embodiment has an arcuate shape mimics the shape of a denture arch.

Figure 3:
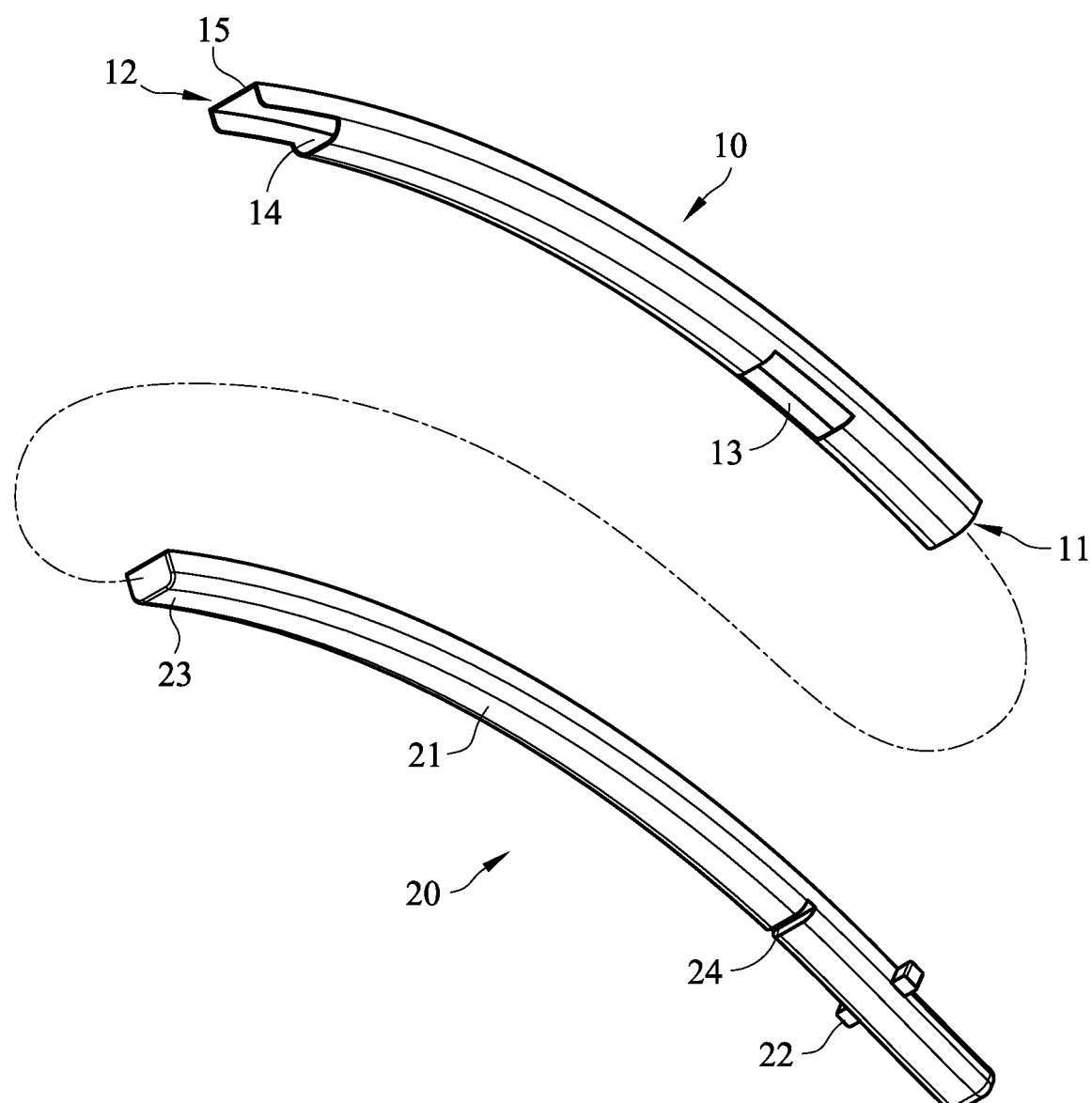
FIG. 3 shows a perspective view of a delivery tool constructed according to a third preferred embodiment of the present invention.

FIG. 3 shows a delivery tool 100 constructed according to a third preferred embodiment of the present invention, which is similar to the second preferred embodiment shown in FIG. 2 except the shape. The delivery tool 100 constructed according to the second and the third preferred embodiments shown in FIGS. 2 and 3 respectively are both similar to the first preferred embodiment shown in FIG. 1, but the shape of the second preferred embodiment is concave down and the shape of the third embodiment preferred embodiment is concave up in comparison with the shape of the first preferred embodiment.

Figure 4:
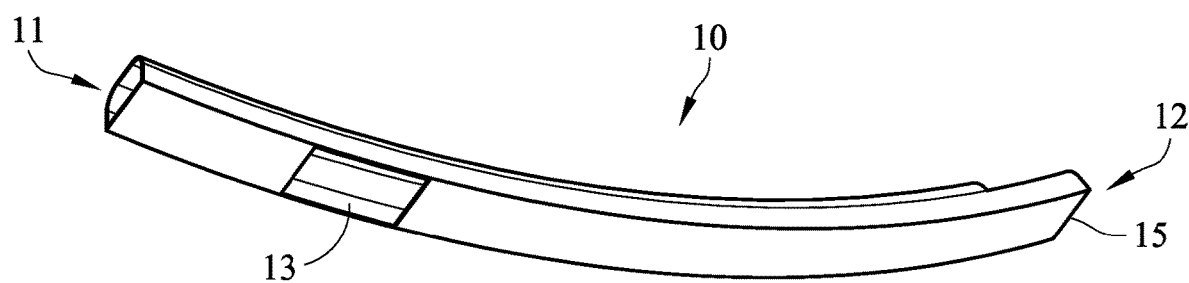
FIG. 4 shows a perspective view of a hollow tube of a delivery tool constructed according to a fourth preferred embodiment of the present invention.
Figure 5:
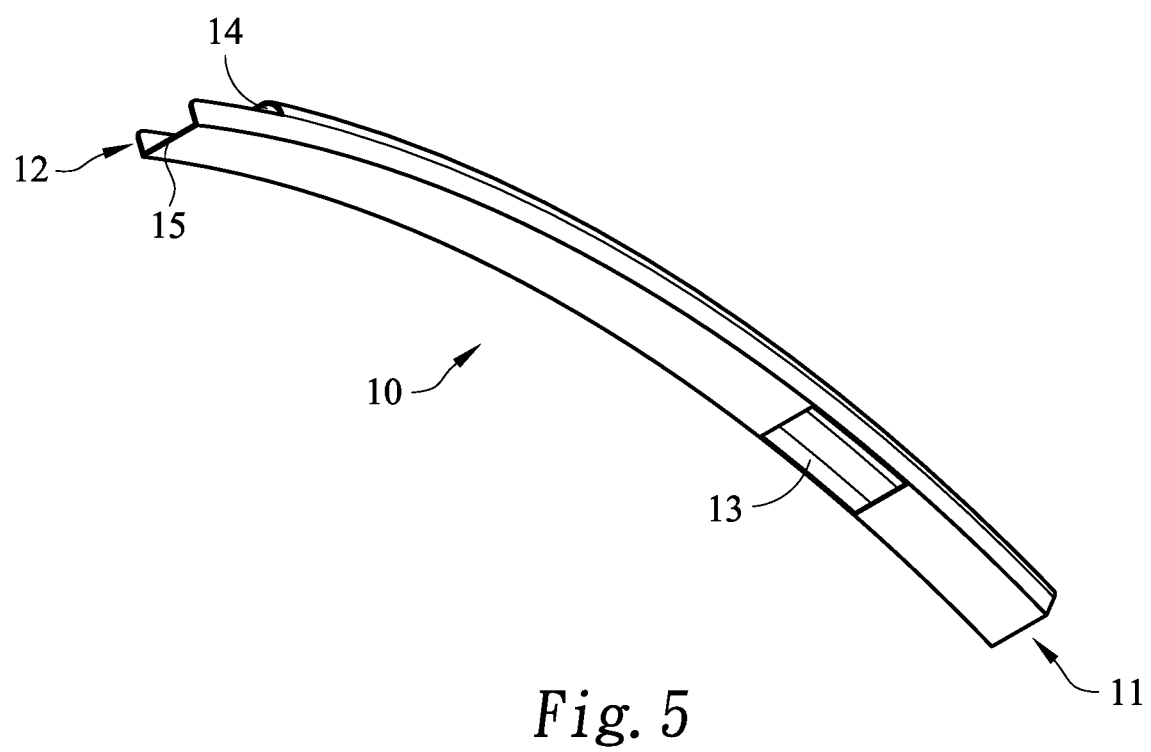
FIG. 5 shows a perspective view of a hollow tube of a delivery tool constructed according to a fifth preferred embodiment of the present invention.

In the fourth and fifth preferred embodiments of the present invention the filler inlet of the hollow tube of the delivery tool is formed on an opposite side of the hollow tube. As shown in FIG. 4, the filler inlet 13 of the hollow tube 10 is formed on the opposite side in comparison with the third preferred embodiment shown in FIG. 3. As shown in FIG. 5, the filler inlet 13 of the hollow tube 10 is formed on the opposite side in comparison with the second preferred embodiment shown in FIG. 2.

The delivery tools shown in the above can be further modified in order to deliver the cement paste or the bone grafts to a site which cannot be reached either by a straight or arcuate hollow tube.

Figure 6:
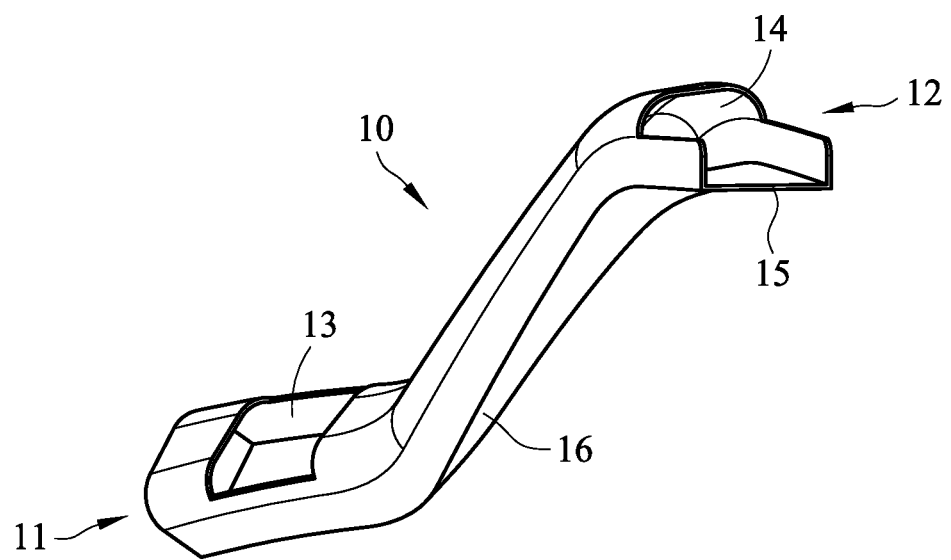
FIG. 6 shows a perspective view of a hollow tube of a delivery tool constructed according to a sixth preferred embodiment of the present invention.
Figure 7:
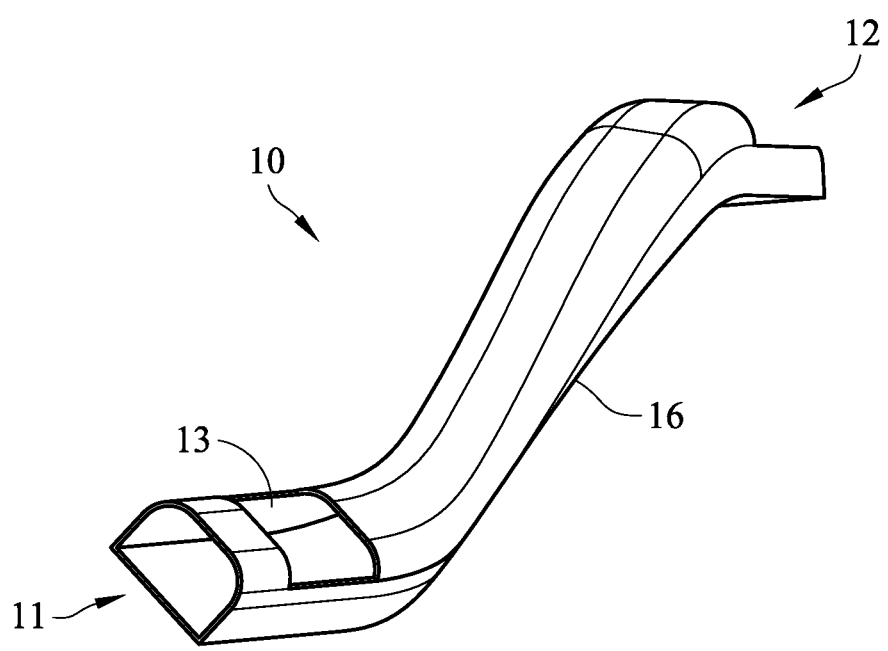
FIG. 7 shows a perspective view of a hollow tube of a delivery tool constructed according to a seventh preferred embodiment of the present invention.

Unlike the straight hollow tube 10 shown in FIG. 1, a hollow tube 10 constructed according to a sixth preferred embodiment of the present invention has a curved and twisted shape. The shape of the hollow tube according to the sixth preferred embodiment is shown in FIG. 6, which can be formed by imagining that the portion containing the filler outlet 12 of the straight hollow tube 10 shown in FIG. 1 is bent upward and rotated about 30 degrees while the other portion containing the filler inlet 13 being held steady. A hollow tube 10 constructed according to a seventh preferred embodiment of the present invention is shown in FIG. 7, which is similar to the sixth preferred embodiment with a rotation angle of about 45 degrees. The plunger 20 as shown in FIG. 6 and FIG. 7 has a slide portion 16 between the filler inlet 13 and the filler out 12.

Figure 8:
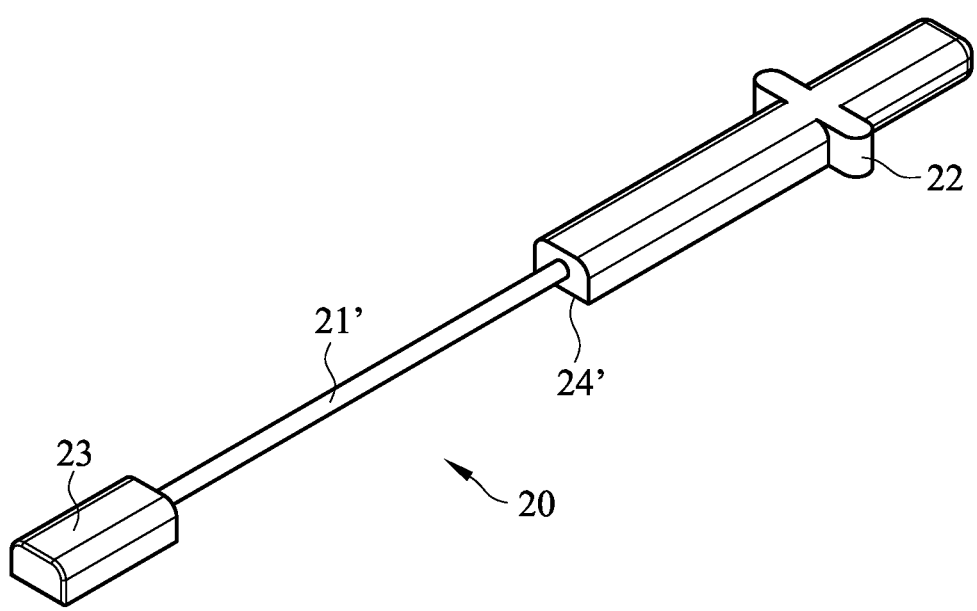
FIG. 8 shows a perspective view of a plunger of a delivery tool constructed according to an eighth preferred embodiment of the present invention.

A plunger suitable for use in the hollow tube 10 shown in FIGS. 6 and 7 must have an insertion portion flexible enough to travel in the curved and twisted hollow tube 10. As shown in FIG. 8, such a plunger 20 has a head 23, and a stop protrusion 22 similar to the plunger 20 shown in FIG. 1, but has a flexible insertion portion 21' with a reduced cross-sectional area between the head 23 and a cliff 24' mimics the mark 24 of the plunger 20 in FIG. 1.

The invention claimed is:

1. A method of forming a structure comprising a layer of hardened paste and particles under the layer, the method comprising the following steps:

providing a delivery tool wherein the delivery tool comprises a hollow tube having a channel, wherein the hollow tube comprises a plunger inlet at a proximal end of the hollow tube, a filler outlet at a distal end of the hollow tube having an opening at the distal end of the hollow tube and a U-shaped drain extending from the opening, a filler inlet which is the plunger inlet or is formed at a location closer to the plunger inlet than to the filler outlet and a plunger comprising an insertion portion which has a cross-section substantially similar in size or smaller than a cross-section of the channel of the hollow tube, and the insertion portion has a head at a distal end of the plunger, so that the head of the plunger is able to be inserted into the channel of the hollow tube via the plunger inlet, passing the filler inlet, and then invading the U-shaped drain of the filler outlet with the insertion portion being received in the channel of the hollow tube;

inserting the hollow tube into a tissue, so that the distal end of the hollow tube is under the tissue and an opening space of the U-shaped drain of the filler outlet is facing the tissue;

filling a paste into the channel through the filler inlet;

inserting the insertion portion of the plunger into the channel through the plunger inlet, wherein the head of the insertion portion is first inserted into the channel of the hollow tube via the plunger inlet, pushing the paste in the channel of the hollow tube, until the head of the insertion portion enters the U-shaped drain of the filler outlet, so that the paste is confined in a space between the head and the tissue;

withdrawing the insertion portion of the plunger from the filler outlet of the hollow tube until the head of the insertion portion passes the filler inlet;

filling particles into the channel through the filler inlet; and advancing the head of the insertion portion toward the filler outlet of the hollow tube, so that the particles are pushed into the opening space of the U-shaped drain of the filler outlet, and are under a layer of the paste.

2. The method of claim 1, wherein the filler inlet is formed at a location closer to the plunger inlet than to the filler outlet, and said filler inlet and said U-shaped drain of the filler outlet have a same opening direction.

3. The method of claim 1, wherein the filler inlet is formed at a location closer to the plunger inlet than to the filler outlet, and said filler inlet and said U-shaped drain of the filler outlet have two different opening directions which are opposite to each other.

4. The method of claim 1, wherein the filler inlet is formed at a location closer to the plunger inlet than to the filler outlet, and said filler inlet and said U-shaped drain of the filler outlet have two different opening directions forming an angle of 20 to 160 degrees.

5. The method of claim 1, wherein the hollow tube is straight.

6. The method of claim 1, wherein the hollow tube is arcuate and the channel is arcuate accordingly.

7. The method of claim 1, wherein the hollow tube has two straight portions at the distal end and at the proximal end, and a slide portion connecting the distal end and the proximal end.

8. The method of claim 7, wherein the insertion portion of the plunger has a thin cross section following the head, which is smaller than that of the head.

9. The method of claim 1, wherein the plunger has a stop protrusion adjacent to the insertion portion and away from the head of the insertion portion, the stop protrusion has a cross-section larger than the cross-section of the channel of the hollow tube, so that the head of the insertion portion is in the U-shaped drain of the filler outlet when the stop protrusion reaches the plunger inlet of the hollow tube.

10. The method of claim 9, wherein the plunger has a uniform cross section between the head and the stop protrusion.

11. The method of claim 1, wherein the cross section of the channel is rectangular.

12. The method of claim 1, wherein said withdrawing is carried out after 1-20 minutes following the paste being confined, so that the paste is hardened or partially hardened.

* * * * *